(12) United States Patent
Bentley et al.

(10) Patent No.: US 6,495,659 B2
(45) Date of Patent: Dec. 17, 2002

(54) STERICALLY HINDERED POLY(ETHYLENE GLYCOL) ALKANOIC ACIDS AND DERIVATIVES THEREOF

(75) Inventors: Michael David Bentley, Huntsville, AL (US); Xuan Zhao, Huntsville, AL (US); Xiaoming Shen, Madison, AL (US); Lihong Guo, Huntsville, AL (US)

(73) Assignee: Shearwater Corporation, Huntsville, AL (US)

( * ) Notice: Subject to any disclaimer, the term of this patent is extended or adjusted under 35 U.S.C. 154(b) by 0 days.

(21) Appl. No.: 09/741,933

(22) Filed: Dec. 20, 2000

(65) Prior Publication Data

US 2002/0002250 A1 Jan. 3, 2002

Related U.S. Application Data

(60) Provisional application No. 60/171,784, filed on Dec. 22, 1999.

(51) Int. Cl.[7] ............................................. C08G 65/34
(52) U.S. Cl. ..................... 528/425; 528/271; 424/193.1; 424/194.1
(58) Field of Search .................. 528/271, 425; 424/193.1, 194.1

(56) References Cited

U.S. PATENT DOCUMENTS 5,614,549 A * 3/1997 Greenwald et al.
5,672,662 A * 9/1997 Harris et al.
5,840,900 A * 11/1998 Greenwald et al.

FOREIGN PATENT DOCUMENTS

| WO | WO 97/03106 | 1/1997 |
| WO | WO 99/45964 | 9/1999 |

OTHER PUBLICATIONS

Higashimura et al; "Watre soluble amphiphilic poly(alkenyl ethers) with hydroxylated side chains", Chem Abstract 109: 111106.*

Topchiyeva, I.N., "Synthesis of Biologically Active Polyethylene Glycol Derivatives. A Review", *Polymer Science U.S.S.R.,* 1990, pp. 833–851, vol. 32, No. 5.

Fradet, et al., "Synthesis of Monocarboxylic Polyoxyethylenes", *Polymer Bulletin,* Feb. 1981, pp. 205–210, vol. 4., No. 4.

* cited by examiner

*Primary Examiner*—Duc Truong
(74) *Attorney, Agent, or Firm*—Alston & Bird LLP

(57) ABSTRACT

The invention provides a sterically hindered polymer that comprises a water-soluble and non-peptidic polymer backbone having at least one terminus covalently bonded to an alkanoic acid or alkanoic acid derivative, wherein the carbon adjacent to the carbonyl group of the acid or acid derivative group has an alkyl or aryl group pendent thereto. The steric effects of the alkyl or aryl group allow greater control of the hydrolytic stability of polymer derivatives. The polymer backbone may be poly(ethylene glycol).

29 Claims, No Drawings

STERICALLY HINDERED POLY(ETHYLENE GLYCOL) ALKANOIC ACIDS AND DERIVATIVES THEREOF

CROSS-REFERENCE TO RELATED APPLICATIONS

This application claims the benefit of U.S. Provisional Application No. 60/171,784, filed Dec. 22, 1999, which is herein incorporated by reference in its entirety.

FIELD OF THE INVENTION

This invention generally relates to water-soluble and non-peptidic polymers, and methods of controlling the hydrolytic properties of such polymers.

BACKGROUND OF THE INVENTION

Covalent attachment of the hydrophilic polymer poly (ethylene glycol), abbreviated PEG, also known as poly (ethylene oxide), abbreviated PEO, to molecules and surfaces is of considerable utility in biotechnology and medicine. In its most common form, PEG is a linear polymer terminated at each end with hydroxyl groups:

$HO-CH_2CH_2O-(CH_2CH_2O)_n-CH_2CH_2-OH$

The above polymer, alpha-,omega-dihydroxylpoly (ethylene glycol), can be represented in brief form as HO—PEG—OH where it is understood that the —PEG— symbol represents the following structural unit:

$-CH_2CH_2O-(CH_2CH_2O)_n-CH_2CH_2-$ where n typically ranges from about 3 to about 4000.

PEG is commonly used as methoxy—PEG—OH, or mPEG in brief, in which one terminus is the relatively inert methoxy group, while the other terminus is a hydroxyl group that is subject to ready chemical modification. The structure of mPEG is given below.

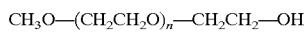
$CH_3O-(CH_2CH_2O)_n-CH_2CH_2-OH$

Random or block copolymers of ethylene oxide and propylene oxide, shown below, are closely related to PEG in their chemistry, and they can be substituted for PEG in many of its applications.

$HO-CH_2CHRO(CH_2CHRO)_nCH_2CHR-OH$ wherein each R is independently H or $CH_3$.

To couple PEG to a molecule, such as a protein, it is often necessary to "activate" the PEG by preparing a derivative of the PEG having a functional group at a terminus thereof. The functional group is chosen based on the type of available reactive group on the molecule that will be coupled to the PEG. For example, the functional group could be chosen to react with an amino group on a protein in order to form a PEG-protein conjugate.

PEG is a polymer having the properties of solubility in water and in many organic solvents, lack of toxicity, and lack of immunogenicity. One use of PEG is to covalently attach the polymer to insoluble molecules to make the resulting PEG-molecule "conjugate" soluble. For example, it has been shown that the water-insoluble drug paclitaxel, when coupled to PEG, becomes water-soluble. Greenwald, et al., *J Org. Chem.*, 60:331–336 (1995).

The prodrug approach, in which drugs are released by degradation of more complex molecules (prodrugs) under physiological conditions, is a powerful component of drug delivery. Prodrugs can, for example, be formed by bonding PEG to drugs using linkages which are degradable under physiological conditions. The lifetime of PEG prodrugs in vivo depends upon the type of functional group linking PEG to the drug. In general, ester linkages, formed by reaction of PEG carboxylic acids or activated PEG carboxylic acids with alcohol groups on the drug, hydrolyze under physiological conditions to release the drug, while amide and carbamate linkages, formed from amine groups on the drug, are stable and do not hydrolyze to release the free drug.

Use of certain activated esters of PEG, such as N-hydroxylsuccinimide esters, can be problematic because these esters are so reactive that hydrolysis of the ester takes place almost immediately in aqueous solution. It has been shown that hydrolytic delivery of drugs from PEG esters can be favorably controlled to a certain extent by controlling the number of linking methylene groups in a spacer between the terminal PEG oxygen and the carbonyl group of the attached carboxylic acid or carboxylic acid derivative. For example, Harris et al., in U.S. Pat. No. 5,672,662, describe PEG butanoic acid and PEG propanoic acid (shown below), and activated derivatives thereof, as alternatives to carboxymethyl PEG (also shown below) when less hydrolytic reactivity in the corresponding ester derivatives is desirable.

$PEG-OCH_2CH_2CH_2CO_2H$

PEG butanoic acid

$PEG-O-CH_2CH_2CO_2H$

PEG propanoic acid

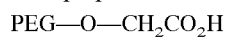
$PEG-O-CH_2CO_2H$

carboxymethyl PEG

In aqueous buffers, hydrolysis of esters of these modified PEG acids can be controlled in a useful way by varying the number of —$CH_2$— spacers between the carboxyl group and the PEG oxygen.

There remains a need in the art for further methods of controlling the hydrolytic degradation of activated polymer derivatives.

SUMMARY OF THE INVENTION

The invention provides a group of water-soluble and non-peptidic polymers having at least one terminal carboxylic acid or carboxylic acid derivative group. The acid or acid derivative group of the polymer is sterically hindered by the presence of an alkyl or aryl group on the carbon adjacent to the carbonyl group of the carboxylic acid ($\alpha$-carbon). The steric effect of the alkyl or aryl group enables greater control of the rate of hydrolytic degradation of polymer derivatives. For example, both activated carboxylic acid derivatives, such as succinimidyl esters, and biologically active polymer conjugates resulting from the coupling of the polymers of the invention to biologically active agents, such as small drug molecules, enzymes or proteins, are more hydrolytically stable due to the presence of the $\alpha$-carbon alkyl or aryl group.

The sterically hindered polymers of the invention comprise a water-soluble and non-peptidic polymer backbone having at least one terminus, the terminus being covalently bonded to the structure

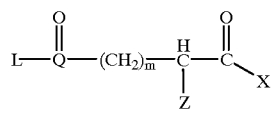

wherein:
L is the point of bonding to the terminus of the polymer backbone;
Q is O or S;
m is 0 to about 20;
Z is selected from the group consisting of alkyl, substituted alkyl, aryl and substituted aryl; and
X is a leaving group.

Examples of suitable water-soluble and non-peptidic polymer backbones include poly(alkylene glycol), poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof In one embodiment, the polymer backbone is poly(ethylene glycol) having an average molecular weight from about 200 Da to about 100,000 Da.

Examples of the Z moiety include methyl, ethyl, n-propyl, isopropyl, n-butyl, isobutyl, sec-butyl, t-butyl, and benzyl. In one embodiment, Z is a $C_1$–$C_8$ alkyl or substituted alkyl.

The leaving group, X, can be, for example, halogen, such as chlorine or bromine, N-succinimidyloxy, sulfo-N-succinimidyloxy, 1-benzotriazolyloxy, hydroxyl, 1-imidazolyl, and p-nitrophenyloxy.

The invention also includes biologically active conjugates of the polymers of the invention and biologically active agents and methods of making such conjugates.

By changing the length or size of the alkyl or aryl group used as the Z moiety, the polymers of the invention offer an increased ability to control and manipulate the hydrolytic stability of polymer derivatives prepared using the polymers. Better control of the rate of hydrolytic degradation enables the practitioner to tailor polymer constructs for specific end uses that require certain degradation properties.

DETAILED DESCRIPTION OF THE INVENTION

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate that the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react. For example, as would be understood in the art, the term "active ester" would include those esters that react readily with nucleophilic groups such as amines. Typically, an active ester will react with an amine in aqueous medium in a matter of minutes, whereas certain esters, such as methyl or ethyl esters, require a strong catalyst in order to react with a nucleophilic group.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, perhaps even indefinitely. Hydrolytically unstable or degradable linkages means that the linkages are degradable in water or in aqueous solutions, including for example, blood. Enzymatically unstable or degradable linkages means that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include carbonate linkages; imine linkages resulted from reaction of an amine and an aldehyde (see, e.g., Ouchi et al., *Polymer Preprints,* 38(1):582–3 (1997), which is incorporated herein by reference.); phosphate ester linkages formed by reacting an alcohol with a phosphate group; hydrozone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, e.g., at an end of a polymer such as PEG, and a carboxyl group of a peptide; and oligonucleotide linkages formed by a phosphoramidite group, e.g., at the end of a polymer, and a 5' hydroxyl group of an oligonucleotide.

The term "biologically active molecule", "biologically active moiety" or "biologically active agent" when used herein means any substance which can affect any physical or biochemical properties of a biological organism, including but not limited to viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, antiviral agents, anti-inflammatory agents, anti-tumor agents, cardiovascular agents, anti-anxiety agents, hormones, growth factors, steroidal agents, and the like.

The terms "alkyl," "alkene," and "alkoxy" include straight chain and branched alkyl, alkene, and alkoxy, respectively. The term "lower alkyl" refers to C1–C6 alkyl. The term "alkoxy" refers to oxygen substituted alkyl, for example, of the formulas —OR or -ROR$^1$, wherein R and R$^1$ are each independently selected alkyl. The terms "substituted alkyl" and "substituted alkene" refer to alkyl and alkene, respectively, substituted with one or more non-interfering substituents, such as but not limited to, C3–C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents.

"Non-interfering substituents" are those groups that yield stable compounds. Suitable non-interfering substituents or radicals include, but are not limited to, halo, $C_1$–$C_{10}$ alkyl, $C_2$–$C_{10}$ alkenyl, $C_2$–$C_{10}$ alkynyl, $C_1$–$C_{10}$ alkoxy, $C_7$–$C_{12}$ aralkyl, $C_7$–$C_{12}$ alkaryl, $C_3$–$C_{10}$ cycloalkyl, $C_3$–$C_{10}$ cycloalkenyl, phenyl, substituted phenyl, toluoyl, xylenyl, biphenyl, $C_2$–$C_{12}$ alkoxyalkyl, $C_7$–$C_{12}$ alkoxyaryl, $C_7$–$C_{12}$ aryloxyalkyl, $C_6$–$C_{12}$ oxyaryl, $C_1$–$C_6$ alkylsulfinyl, $C_1$–$C_{10}$ alkylsulfonyl, —$(CH_2)_m$—O—($C_1$–$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$–$C_{10}$ alkyl), —C(O)— ($C_1$–$C_{10}$ alkyl), $C_2$–$C_{10}$ thioalkyl, —C(O) O—($C_1$–$C_{10}$ alkyl), —OH, —$SO_2$, =S, —COOH, —$NR_2$, carbonyl, —C(O)—($C_1$–$C_{10}$ alkyl)—$CF_3$, —C(O)—$CF_3$, —C(O)$NR_2$, —($C_1$–$C_{10}$ alkyl)—S—($C_6$–$C_{12}$ aryl), —C(O)—($C_6$–$C_{12}$ aryl), —$(CH_2)_m$—O—$(CH_2)_m$—O—($C_1$–$C_{10}$ alkyl) wherein each m is from 1 to 8, —C(O)$NR_2$, —C(S)$NR_2$, —$SO_2NR_2$, —NRC(O)$NR_2$, —NRC(S)$NR_2$, salts thereof, and the like. Each R as used herein is H, alkyl or substituted alkyl, aryl or substituted aryl, aralkyl, or alkaryl.

The invention provides a sterically hindered polymer, comprising a water-soluble and non-peptidic polymer backbone having at least one terminus, the terminus being covalently bonded to the structure Formula I

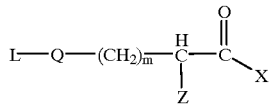

wherein:
L is the point of bonding to the terminus of the polymer backbone;
Q is O or S;
m is 0 to about 20;
Z is selected from the group consisting of alkyl, substituted alkyl, aryl and substituted aryl; and
X is a leaving group.

The polymer backbone of the water-soluble and non-peptidic polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG, or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—$(CH_2CH_2O)_n$—$CH_2CH_2$—, where n is from about 3 to about 4000, typically from about 3 to about 2000, is one useful polymer in the practice of the invention. PEG having a molecular weight of from about 200 Da to about 100,000 Da are particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly (ethylene glycol) can be represented in general form as R(—PEG—OH)$_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Branched PEG can also be in the form of a forked PEG represented by PEG (—YCH$Z_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

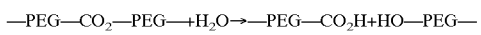

It is understood by those skilled in the art that the term poly(ethylene glycol) or PEG represents or includes all the above forms.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly (hydroxypropylmethacrylamide), poly(α-hydroxy acid), poly(vinyl alcohol), polyphosphazene, polyoxazoline, poly (N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

Those of ordinary skill in the art will recognize that the foregoing list for substantially water soluble and non-peptidic polymer backbones is by no means exhaustive and is merely illustrative, and that all polymeric materials having the qualities described above are contemplated.

Examples of suitable alkyl and aryl groups for the Z moiety include methyl, ethyl, n-propyl, isopropyl, n-butyl, isobutyl, sec-butyl, t-butyl, and benzyl. In one embodiment, Z is a $C_1$–$C_8$ alkyl or substituted alkyl.

The optional $CH_2$ spacer between the α-carbon and the Q moiety can provide additional dampening effect on the rate of hydrolytic degradation of the molecule. In one embodiment, m is 1 to about 10.

The X moiety is a leaving group, meaning that it can be displaced by reaction of a nucleophile with the molecule containing X. In some cases, as when X is hydroxy, the group must be activated by reaction with a molecule such as N,N'-dicyclohexylcarbodiimide (DCC) in order to make it an effective leaving group. Examples of suitable X moieties include halogen, such as chlorine and bromine, N-succinimidyloxy, sulfo-N-succinimidyloxy, 1-benzotriazolyloxy, hydroxyl, 1-imidazolyl, and p-nitrophenyloxy. In one aspect, the polymer has a terminal carboxylic acid group (i.e. X is hydroxyl).

In one embodiment, the polymer of the invention has the structure

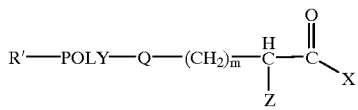

wherein:

POLY is a water-soluble and non-peptidic polymer backbone, such as PEG;

R' is a capping group; and

Q, m, Z and X are as defined above.

R' can be any suitable capping group known in the art for polymers of this type. For example, R' can be a relatively inert capping group, such as an alkoxy group (e.g. methoxy).

Alternatively, R' can be a functional group. Examples of suitable functional groups include hydroxyl, protected hydroxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate. The functional group is typically chosen for attachment to a functional group on a biologically active agent. As would be understood, the selected R' moiety should be compatible with the X group so that reaction with X does not occur.

As would be understood in the art, the term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl or ethyl. Other protecting groups known in the art may also be used in the invention.

Specific examples of terminal functional groups in the literature include N-succinimidyl carbonate (see e.g., U.S. Pat. Nos. 5,281,698, 5,468,478), amine (see, e.g., Buckmann et al. *Makromol. Chem.* 182:1379 (1981), Zaplipsky et al. *Eur. Polym. J* 19:1177 (1983)), hydrazide (See, e.g., Andresz et al. *Makromol. Chem.* 179:301 (1978)), succinimidyl propionate and succinimidyl butanoate (see, e.g., Olson et al. *in Poly(ethylene glycol) Chemistry & Biological Applications*, pp 170–181, Harris & Zaplipsky Eds., ACS, Washington, DC, 1997; see also U.S. Pat. No. 5,672,662), succinimidyl succinate (See, e.g., Abuchowski et al. *Cancer Biochem. Biophys.* 7:175 (1984) and Joppich et al. *Macrolol. Chem.* 180:1381 (1979), succinimidyl ester (see, e.g., U.S. Pat. No. 4,670,417), benzotriazole carbonate (see, e.g., U.S. Pat. No. 5,650,234), glycidyl ether (see, e.g, Pitha et al. *Eur. J Biochem.* 94:11 (1979), Elling et al., *Biotech. Appl. Biochem.* 13:354 (1991), oxycarbonylimidazole (see, e.g., Beauchamp, et al., *Anal. Biochem.* 131:25 (1983), Tondelli et al. *J. Controlled Release* 1:251 (1985)), p-nitrophenyl carbonate (see, e.g., Veronese, et al., *Appl. Biochem. Biotech.,* 11: 141 (1985); and Sartore et al., *Appl. Biochem. Biotech.,* 27:45 (1991)), aldehyde (see, e.g., 20 Harris et al. *J Polym. Sci. Chem. Ed.* 22:341 (1984), U.S. Pat. No. 5,824,784, U.S. Pat. No. 5,252,714), maleimide (see, e.g., Goodson et al. *Bio/Technology* 8:343 (1990), Romani et al. in *Chemistry of Peptides and Proteins* 2:29 (1984)), and Kogan, *Synthetic Comm.* 22:2417 (1992)), orthopyridyl-disulfide (see, e.g., Woghiren, et al. *Bioconj. Chem.* 4:314 (1993)), acrylol (see, e.g., Sawhney et al., *Macromolecules,* 26:581 (1993)), vinylsulfone (see, e.g., U.S. Pat. No. 5,900, 461). In addition, two molecules of the polymer of this invention can also be linked to the amino acid lysine to form a di-substituted lysine, which can then be further activated with N-hydroxysuccinimide to form an active N-succinimidyl moiety (see, e.g., U.S. Pat. No. 5,932,462). All of the above references are incorporated herein by reference.

R' can also have the structure -W-D, wherein W is a linker and D is a biologically active agent. Alternatively, the polymer structure can be a homobifunctional molecule such that R' is —Q($CH_2$)$_m$CHZC(O)X, wherein Q, m, Z and X are as defined above.

An example of a multi-arm polymer of the invention is shown below:

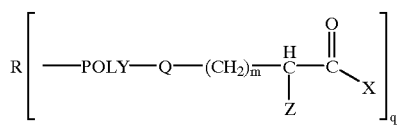

wherein:

POLY is a water-soluble and non-peptidic polymer backbone, such as PEG;

R is a central core molecule, such as glycerol or pentaerythritol;

q is an integer from 2 to about 300; and

Q, m, Z and X are as defined above.

Further examples of the polymers of the invention include polymers of the structure

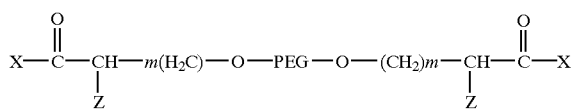

wherein:
PEG is poly(ethylene glycol); and
X, m and Z are as defined above.

The polymers of the invention, whether activated or not, can be purified from the reaction mixture. One method of purification involves precipitation from a solvent in which the polymers are essentially insoluble while the reactants are soluble. Suitable solvents include ethyl ether or isopropanol. Alternatively, the polymers may be purified using ion exchange, size exclusion, silica gel, or reverse phase chromatography.

In all the above embodiments, the presence of the α-alkyl or α-aryl group (Z) confers upon the polymer greater stability to hydrolysis due to the steric and electronic effect of the alkyl or aryl group. The steric effect may be increased by increasing the size of the alkyl or aryl group, as would be the case in replacing methyl with ethyl. In other words, as the number of carbon atoms in Z increases, the rate of hydrolysis decreases. As noted above, use of this steric effect may also be applied in combination with the electronic effect obtained by variation in the distance of the Q moiety from the carboxyl group (i.e. control of the value of m). By controlling both m and Z, the rate of hydrolysis can be regulated in a more flexible manner.

Since the enzyme catalyzed reactions that cause enzymatic degradation involve exact spatial fits between the enzyme active site and the polymer, steric effects can be very important in these reactions as well. The polymers of the invention can also be used to better regulate or control enzymatic degradation in addition to hydrolytic degradation.

When coupled to biologically active agents, the polymers of the invention will help regulate the rate of hydrolytic degradation of the resulting polymer conjugate. As an example, when the polymers of the invention are coupled with alcohols or thiols to form esters or thioesters respectively, the esters or thioesters are more stable to hydrolysis. Thus, a drug bearing an alcohol or thiol group may be derivatized with a polymer of the invention and the hydrolytic release of the drug from such esters or thiolesters can be controlled by choice of the α-alkyl or α-aryl group.

The invention provides a biologically active polymer conjugate comprising a water-soluble and non-peptidic polymer backbone having at least one terminus, the terminus being covalently bonded to the structure

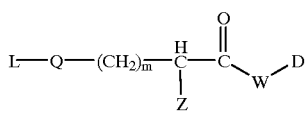

wherein:
L is the point of bonding to the terminus of the polymer backbone;
Q is O or S;
m is 0 to about 20;
Z is selected from the group consisting of alkyl, substituted alkyl, aryl and substituted aryl;
W is a linker; and
D is a biologically active agent.

The linker W is the residue of the functional group used to attach the biologically active agent to the polymer backbone. In one embodiment, W is O, S, or NH.

Examples of suitable biologically active agents include peptides, proteins, enzymes, small molecule drugs, dyes, lipids, nucleosides, oligonucleotides, cells, viruses, liposomes, microparticles and micelles.

The invention also includes a method of preparing biologically active conjugates of the polymers of the invention by reacting a polymer of Formula I with a biologically active agent.

The following examples are given to illustrate the invention, but should not be considered in limitation of the invention.

EXPERIMENTAL

EXAMPLE 1

Preparation of mPEG—O—CH$_2$CH(CH$_3$)CO$_2$H and mPEG—O—CH$_2$CH(CH$_3$)CO$_2$NS (NS=N-succinimidyl)

Reactions:

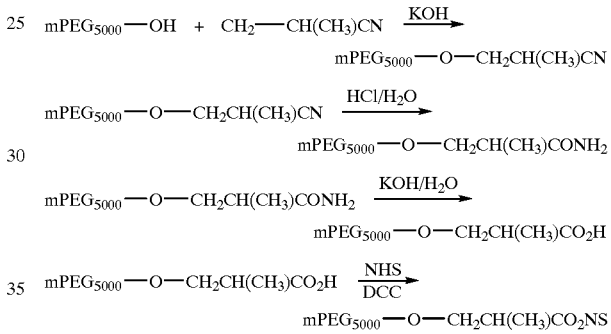

1. Preparation of mPEG$_{5000}$—O—CH$_2$CH(CH$_3$)CN

MPEG$_{5000}$OH (4.0 g) and methacrylonitrile (1.0 ml) were stirred for three days at room temperature in a mixture of benzene (5.0 ml), dichloromethane (6.5 ml), and KOH (50% in H$_2$O; 0.15 ml). To the resulting mixture was added 200 ml of 10% aqueous NaH$_2$PO$_4$. The mixture was stirred for 10 minutes before extracting with 200 ml of dichloromethane (100+50+50 ml). The organic phase was dried over MgSO$_4$, concentrated, and precipitated into ethyl ether (50 ml). The precipitate was collected by filtration and dried under vacuum at room temperature to obtain 3.17 g of white powder. NMR: (dmso-d6, ppm): 1.0438 (d, α—CH$_3$); 2.55 (m, CH); 3.51 (br m, PEG—CH$_2$CH$_2$—O—).

2. Preparation of mPEG$_{5000}$—O—CH$_2$CH(CH$_3$)CONH$_2$ mPEG$_{5000}$—O—CH$_2$CH(CH$_3$)CN (3.17 g) was dissolved in 14 ml of concentrated HCl and the solution was stirred three days at room temperature. The resulting solution was diluted to 300 ml with water and 45 g of NaCl was added. The product was extracted with dichloromethane (3×100 ml) and the extract dried over MgSO$_4$. The solution was concentrated and the product precipitated in ethyl ether (50 ml). The product was collected by filtration and dried under vacuum at room temperature to obtain 2.6 g of white powder. NMR (dmso-d6, ppm): 0.714 (d, α—H$_3$); 3.51 (br m, PEG —CH$_2$CH$_2$—O—).

3. Preparation of mPEG$_{5000}$—O—CH$_2$CH(CH$_3$)CO$_2$H

A solution of 2.6 g of mPEG$_{5000}$—O—CH$_2$CH(CH$_3$)CONH$_2$ in 100 ml of 8% KOH was stirred at room temperature for three days and the pH was then adjusted to 2.0 with HCl. The product was extracted with 100 ml of methylene chloride and the extract dried over $MgSO_4$. The solution was then concentrated and the product precipitated by addition to 200 ml of ethyl ether. The product was collected by filtration and dried under vacuum at room temperature to obtain 1.7 g of white powder. The product was further purified by chromatography on DEAE sepharose with the column first eluted with water and then with 1 M NaCl. The product was extracted from the NaCl eluent with methylene chloride and the organic layer dried over $MgSO_4$. The methylene chloride solution was concentrated and the product precipitated from about 30 ml of ethyl ether. It was collected by filtration, and dried under vacuum at room temperature to obtain 0.8 g of white powder. Gel permeation chromatography on Ultrahydrogel 250 displayed a single peak.

$^1$H NMR (dmso-d6, ppm): 1.035 (d, α—$H_3$); 2.55 (m, CH); 3.51 (br m, PEG backbone $CH_2$). The integral ratio of the PEG backbone protons to that of the alpha methyl protons indicated 100% substitution.

4. Preparation of $CH_3$—O—$PEG_{5000}$—O—$CH_2CH(CH_3)$ $CO_2NS$ (NS=N-succinimidyl)

$CH_3$—O—$PEG_{5000}$—O—$CH_2CH(CH_3)CO_2H$ (0.6 g) was dissolved in 50 ml of methylene chloride, N-hydroxysuccinimide (0.0144 g) and N,N-dicyclohexylcarbodiimide (0.026) in 2 ml of methylene chloride was added. After stirring overnight, the mixture was filtered and the filtrate concentrated under vacuum. The product was precipitated by addition of the filtrate to isopropanol, then collected by filtration and dried under vacuum to yield 0.4 g of white powder. Comparison of integration of the PEG backbone protons with those on the NS group indicated 100% substitution.

$^1$H NMR (ppm, dmso-d6): 1.20 (d, C$\underline{H}_3$—CH); 2.81 (s, NS); 3.51 (br m, PEG —$CH_2CH_2$—O—).

EXAMPLE 2

Preparation of mPEG—O—$CH_2CH_2CH(CH_3)$ $CO_2H$ and mPEG—O—$CH_2CH_2CH(CH_3)CO_2NS$ Reactions:

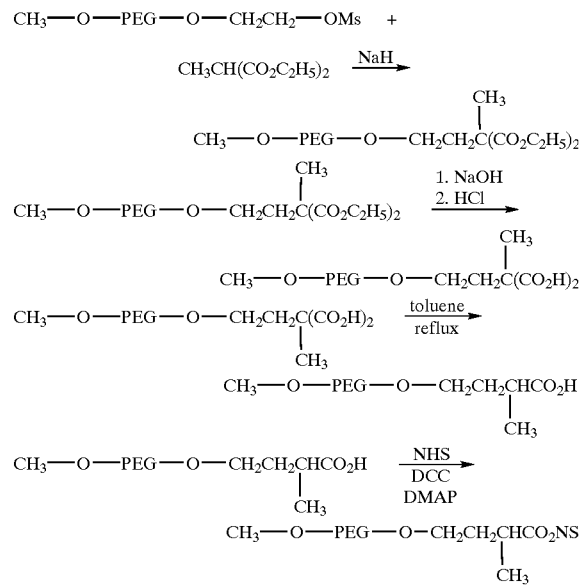

1. Preparation of $CH_3$—O—PEG—O—$CH_2CH_2C(CH_3)$ $(CO_2H)_2$

Diethyl methylmalonate (9.6 ml) in 150 ml of dry dioxane was added dropwise to NaH (2.4 g) in 60 ml of toluene under argon. $MPEG_{5000}$ mesylate (30 g) in 250 ml of toluene was azeotropically distilled to remove 150 ml of toluene and the residue was added to the above diethyl methylmalonate solution. After refluxing the mixture for 3–4 hours, it was evaporated under vacuum to dryness and dried in vacuo overnight. The dried material was then dissolved in 200 ml of 1N NaOH, the solution was stirred for 2 days at room temperature, and the pH adjusted to 3 with 1N HCl. NaCl was added to the solution to a concentration of about 15% and the mixture was then extracted with 350 ml of $CH_2Cl_2$ in several portions. The combined extracts were dried over $Na_2SO_4$, concentrated under vacuum and the product precipitated by addition of isopropanol/ether (1:1). The product was collected by filtration and dried under vacuum overnight to obtain 24.7 g of product as a white powder. GPC (Ultrahydrogel 250) showed the product to be 98% pure.

$^1$H NMR (dmso-d6, ppm): 1.27 (s, $CH_3$—C); 1.96 (t, $CH_2C$ $\underline{H}_2$—C); 3.51 (br m, PEG—$CH_2CH_2$—O—).

2. Preparation of $CH_3$—O—$PEG_{5000}$—O—$CH_2CH_2CH$ $(CH_3)CO_2H$ $CH_3$—O—$PEG_{5000}$—O—$CH_2CH_2C(CH_3)(CO_2H)_2$ (20 g) was dissolved in 300 ml of toluene and the resulting solution was refluxed for 3 hours. The solution was then concentrated under vacuum and the residue precipitated with isopropanol/ether (1:1), collected by filtration, and dried under vacuum overnight to obtain 18.8 g of white powder. GPC (Ultrahydrogel 250) indicated the product to be 95% pure.

$^1$H NMR(dmso-d6, ppm): 1.061 (d, C$\underline{H}_3$—CH); 2.40 (q, CH); 1.51 (m, C$\underline{H}_2$—CH); 1.80 (m, C$\underline{H}_2$—$CH_2$—CH); 3.51 (br m, PEG —$CH_2CH_2$—O—).

3. Preparation of $CH_3$—O—$PEG_{5000}$—O—$CH_2CH_2CH$ $(CH_3)CO_2NS$ (NS=N-succinimidyl)

$CH_3$—O—$PEG_{5000}$—O—$CH_2CH_2CH(CH_3)CO_2H$ (3.8 g) was dissolved in 40 ml of methylene chloride and N-hydroxysuccinimide (0.094 g, 1.07 equiv.) and N,N-dicyclohexylcarbodiimide (0.166 g, 1.07 equiv.) in 3 ml of methylene chloride was added. After stirring overnight, the mixture was filtered and the filtrate concentrated under vacuum. The product was precipitated by addition of the filtrate to a 1:1 mixture of isopropanol and ethyl ether then collected by filtration and dried under vacuum to yield 3.2 g of white powder. Comparison of integration of the PEG backbone protons with those on the NS group indicated >95% substitution.

$^1$H NMR (ppm, dmso-d6): 1.235 (d, C$\underline{H}_3$CH—); 1.76 (m, 1.90 m, —O—$CH_2C\underline{H}_2$CH—); 2.81 (s, $CH_2CH_2$ on NS;) 2.91 (m, —O—$CH_2CH_2C\underline{H}$—); 3.51 (br m, PEG —$CH_2CH_2$—O—).

EXAMPLE 3

PEGylation of Lysozyme with Activated α-Alkylalkanoic acids

To 4 ml of lysozyme solution (3 mg/ml) in 50 pH 6.5 buffer (50 mM sodium phosphate/50 mM NaCl ) was added 20 mg of the N-succinimidyl ester of the PEG alkanoate and the progress of the reaction at 22° C. was monitored by capillary electrophoresis at a wavelength of 205 nm. The area of the peak corresponding to unreacted protein was plotted against time and the half-life of the lysozyme in the PEGylation reaction was determined from that plot. The half-life using N-succinimidyl $mPEG_{5K}$ α-methylpropanoate was 100 minutes, while that of N-succinimidyl $mPEG_{5K}$ α-methylbutanoate was 120 minutes. The half-life for PEGylation using either of the non-α-alkylated analogues, mPEG$_{5K}$ N-succinimidyl propanoate or mPEG$_{5K}$ N-succinimidyl butanoate, was 30 minutes.

EXAMPLE 4

Hydrolysis Rates of N-Succinimidyl mPEG α-Alkylalkanoates

Hydrolysis studies were conducted at pH 8.1 and 25° C. In a typical experiment, 1–2 mg of the N-succinimidyl ester of the PEG alkanoate or PEG α-alkylalkanoate were dissolved in 3 ml of buffer and transferred to a cuvette. The absorbance at 260 nm was monitored using a Molecular Devices SpectraMax Plus uv-visible spectrophotometer. The hydrolytic half-life was determined from the first-order kinetic plot. For N-succinimidyl mPEG$_{5K}$ α-methylpropanoate and N-succinimidyl mPEG$_{5K}$ α-methylbutanoate, the half-lives for hydrolysis were 33 minutes and 44 minutes respectively, while for the corresponding non-alkylated analogue, N-succinimidyl mPEG$_{5K}$ propanoate and mPEG$_{5K}$ butanoate, the half-life was 20 minutes.

EXAMPLE 5

8-arm-PEG$_{20KDa}$-Quinidine α-methylbutanoate 8-arm-PEG$_{20KDa}$ α-methyl butanoic acid (2.0 g, 0.1 mmol) was azeotropically dried in vacuo with CHCl$_3$ (3×50 ml) and was redissolved in CH$_2$Cl$_2$ (25.0 ml). To this clear solution was added quinidine (0.50 g, 1.5 mmol), DMAP (0.15 g, 1.2 mmol), and HOBt (cat.). DCC (0.310 g, 1.5 mmol in 1 ml of CH$_2$Cl$_2$) was then added and the mixture was allowed to stir at room temperature under argon for 17 h. The mixture was then concentrated in vacuo and the residual syrup was dissolved in toluene (100 ml) and filtered through a plug of Celite. The toluene was removed in vacuo at 45° C. and the residue was treated with 5 ml of CH$_2$Cl$_2$ and triturated with 2-propanol (300 ml). Further drying in vacuo afforded a pure product (2.0 g, 99%) with 100% substitution as indicated by $^1$H NMR.

EXAMPLE 6

Hydrolysis Study of 8-arm-PEG$_{20KDa}$-Quinidine α-methylbutanoate By Reverse Phase HPLC A C-18 column (Betasil C18, 100×2, 5 μm, Keystone Scientific) was used in a HP-1100 HPLC system. Eluent A was 0.1% TFA in water, while eluent B was acetonitrile.

For the hydrolysis study in pure buffer, the quinidine conjugate was dissolved in 10 mM phosphate buffer for a final concentration of 8 mg/ml. The resulting solution was pipetted into sealed vials (0.2 ml each) at 37° C. At timed intervals, a vial was taken and to it was added 0.2 ml of acetonitrile. After filtration, the sample was analyzed by RP-HPLC with UV detector at wavelength of 228 nm. Least squares kinetic treatment of the data yielded a half-life of 46 hours for hydrolysis.

EXAMPLE 7

(Pivaloyloxy)methyl mPEG$_{5KDa}$-α-methylbutanoate mPEG$_{5KDa}$ α-methylbutanoic acid (16.8 g, 3.4 mmol) was dissolved in acetonitrile (500 ml) and was concentrated in vacuo to about 100 ml. Dichloromethane (100 ml) was added under argon and the solution was allowed to stir at room temperature. To this clear, colorless solution was added DBU (2.4 mL, 16.2 mmol) followed by chloromethyl pivalate (2.4 ml, 16.6 mmol). The solution was allowed to stir at room temperature under argon for 17 h. The solution was then concentrated to dryness, dissolved in 2-propanol (300 ml), and cooled in an ice bath to give a white solid that was collected by filtration. Further drying in vacuo gave (pivaloyloxy)methyl mPEG$_{5KDa}$-α-methylbutanoate (14.5 g, ~86%) as a white solid. $^1$H NMR (dmso-d$_6$, 300 MHz) δ 1.08 (d, 3H, J 7.1 Hz, OCH$_2$CH$_2$CH(CH$_3$)COPOM), 1.14 (s, 9H, OCH$_2$CO(CH$_3$)$_3$), 1.55–1.69 (m, 2.8H, OCH$_2$CH$_A$H$_B$CH(CH$_3$)COPOM), 1.73–1.85 (m, 1.3H, OCH$_2$CH$_A$H$_B$CH(CH$_3$)COPOM), 2.49–2.60 (m, OCH$_2$CH$_2$CH—(CH$_3$)COPOM), 3.51 (bs, 454H, PEG backbone), 5.70 (s, 1.9H, COCH$_2$POM) (POM=pivaloyloxymethy).

That which is claimed is:

1. A sterically hindered polymer, comprising a water-soluble and non-peptidic polymer backbone having at least one terminus, said terminus being covalently bonded to the structure.

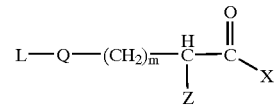

wherein:

L is the point of bonding to the terminus of the polymer backbone;

Q is O or S;

m is 1 to about 20;

Z is selected from the group consisting of alkyl, substituted alkyl, aryl and substituted aryl; and X is a leaving group.

2. The polymer of claim 1, wherein said water-soluble and non-peptidic polymer backbone is selected from the group consisting of poly(alkylene glycol), poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), and copolymers, terpolymers, and mixtures thereof.

3. The polymer of claim 1, wherein the water-soluble and non-peptidic polymer is poly(ethylene glycol).

4. The polymer of claim 3, wherein the poly(ethylene glycol) has an average molecular weight from about 200 Da to about 100,000 Da.

5. The polymer of claim 1, wherein the water-soluble and non-peptidic polymer has from about 2 to about 300 termini.

6. The polymer of claim 1, wherein Z is a C$_1$–C$_8$ alkyl or substituted alkyl.

7. The polymer of claim 1, wherein Z is selected from the group consisting of methyl, ethyl, n-propyl, isopropyl, n-butyl, isobutyl, sec-butyl, t-butyl, and benzyl.

8. The polymer of claim 1, wherein m is 1 to about 10.

9. The polymer of claim 1, wherein X is selected from the group consisting of chlorine, bromine, N-succinimidyloxy, sulfo-N-succinimidyloxy, 1-benzotriazolyloxy, hydroxyl, 1-imidazolyl, and p-nitrophenyloxy.

10. The polymer of claim 1, wherein the polymer has the structure

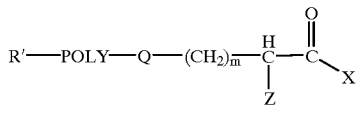

wherein:

POLY is a water-soluble and non-peptidic polymer backbone;

R' is a capping group; and

Q, m, Z and X are as defined above.

11. The polymer of claim 10, wherein R' is methoxy.

12. The polymer of claim 10, wherein R' is a functional group selected from the group consisting of hydroxyl, protected hydroxyl, active ester, active carbonate, acetal, aldehyde, aldehyde hydrates, alkenyl, acrylate, methacrylate, acrylamide, active sulfone, amine, protected amine, hydrazide, protected hydrazide, thiol, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate.

13. The polymer of claim 10, wherein R' is -W-D, wherein W is a linker and D is a biologically active agent.

14. The polymer of claim 10, wherein R' is —Q(CH$_2$)mCHZC(O)X, wherein Q, m, Z and X are as defined above.

15. The polymer of claim 10, wherein POLY is poly(ethylene glycol).

16. The polymer of claim 15, wherein the poly(ethylene glycol) has an average molecular weight from about 200 Da to about 100,000 Da.

17. The polymer of claim 10, wherein Z is a $C_1$–$C_8$ alkyl or substituted alkyl.

18. The polymer of claim 10, wherein Z is selected from the group consisting of methyl, ethyl, n-propyl, isopropyl, n-butyl, isobutyl, sec-butyl, t-butyl, and benzyl.

19. The polymer of claim 10, wherein m is 1 to about 10.

20. The polymer of claim 10, wherein X is hydroxyl.

21. The polymer of claim 1, wherein the polymer has the structure

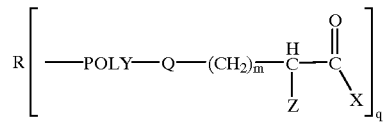

wherein:

POLY is a water-soluble and non-peptidic polymer backbone;

R is a central core molecule;

q is an integer from 2 to about 300; and

Q, m, Z and X are as defined above.

22. The polymer of claim 21, wherein POLY is poly(ethylene glycol).

23. The polymer of claim 22, wherein POLY has an average molecular weight from about 200 Da to about 100,000 Da.

24. The polymer of claim 1, wherein the polymer has the structure

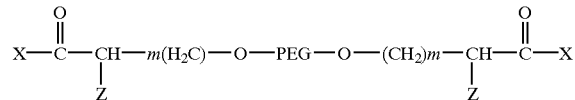

wherein:

PEG is poly(ethylene glycol); and

X, m and Z are as defined above.

25. The polymer of claim 24, wherein X is hydroxyl.

26. The polymer of claim 4, wherein the poly(ethylene glycol) has an average molecular weight from about 6000 Da to about 80,000 Da.

27. The polymer of claim 16, wherein the poly(ethylene glycol) has an average molecular weight from about 6000 Da to about 80,000 Da.

28. The polymer of claim 23, wherein POLY has an average molecular weight from about 6000 Da to about 80,000 Da.

29. The polymer of claim 24, wherein PEG has an average molecular weight from about 6000 Da to about 80,000 Da.

* * * * *

UNITED STATES PATENT AND TRADEMARK OFFICE
CERTIFICATE OF CORRECTION

PATENT NO. : 6,495,659 B2
DATED : December 17, 2002
INVENTOR(S) : Bentley et al.

It is certified that error appears in the above-identified patent and that said Letters Patent is hereby corrected as shown below:

Column 1,
Line 32, the structure should appear as follows:
$-CH_2CH_2O(CH_2CH_2O)_n-CH_2CH_2-$ Column 3,
Line 1, the structure at the top of the column should appear as follows:

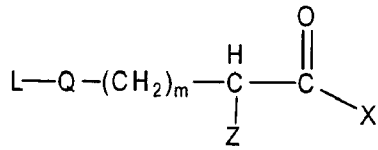

Signed and Sealed this

Twentieth Day of May, 2003

JAMES E. ROGAN
*Director of the United States Patent and Trademark Office*